United States Patent [19]
Katsura

[11] Patent Number: 5,196,166
[45] Date of Patent: Mar. 23, 1993

[54] BLOOD STORAGE TANK
[75] Inventor: Yoshiro Katsura, Fuji, Japan
[73] Assignee: Terumo Kabushiki Kaisha, Tokyo, Japan
[21] Appl. No.: 668,820
[22] Filed: Mar. 8, 1991

Related U.S. Application Data
[63] Continuation of Ser. No. 196,049, May 19, 1988, abandoned.

[30] Foreign Application Priority Data
May 19, 1987 [JP] Japan .................. 62-122243

[51] Int. Cl.$^5$ .................. A61M 1/34
[52] U.S. Cl. .................. 422/45; 422/46; 422/48; 128/DIG. 3; 261/DIG. 28; 604/319; 604/403
[58] Field of Search ............. 422/44, 48; 128/DIG. 3; 261/DIG. 28; 604/319, 403

[56] References Cited
U.S. PATENT DOCUMENTS

| | | | |
|---|---|---|---|
| 3,847,152 | 11/1974 | Schachet | 128/276 |
| 4,061,031 | 12/1977 | Grimsrud | 422/44 X |
| 4,073,622 | 2/1978 | Luppi | 422/47 |
| 4,261,951 | 4/1981 | Milev | 422/46 |
| 4,439,190 | 3/1984 | Protzmann et al. | 604/319 |
| 4,620,965 | 11/1986 | Fukusawa et al. | 422/46 |

FOREIGN PATENT DOCUMENTS

| | | |
|---|---|---|
| 152233 | 7/1953 | Australia . |
| 278207 | 5/1964 | Australia . |
| 75911 | 4/1978 | Australia . |
| 11142/83 | 6/1987 | Australia . |
| 26601/84 | 3/1988 | Australia . |
| 0146708 | 3/1965 | European Pat. Off. . |
| 0072196 | 2/1983 | European Pat. Off. . |
| 0112641 | 7/1984 | European Pat. Off. . |
| 0145158 | 6/1985 | European Pat. Off. . |
| 0283125 | 9/1988 | European Pat. Off. . |
| 0207304 | 8/1989 | European Pat. Off. . |
| 1089125 | 9/1960 | Fed. Rep. of Germany . |
| 2082071 | 3/1982 | United Kingdom . |

Primary Examiner—Lynn M. Kummert
Attorney, Agent, or Firm—Burns, Doane, Swecker & Mathis

[57] ABSTRACT

A blood reservoir has a blood storage section for temporarily storing blood, a blood discharge port defined in a bottom of the blood storage section for discharging the blood, the blood discharge port being displaced from a central portion of the blood storage section, and at least one partition disposed substantially vertically in the blood storage section for suppressing resonant suppression of a surface level of the stored blood upon pulsative blood discharge from the blood storage section.

15 Claims, 6 Drawing Sheets

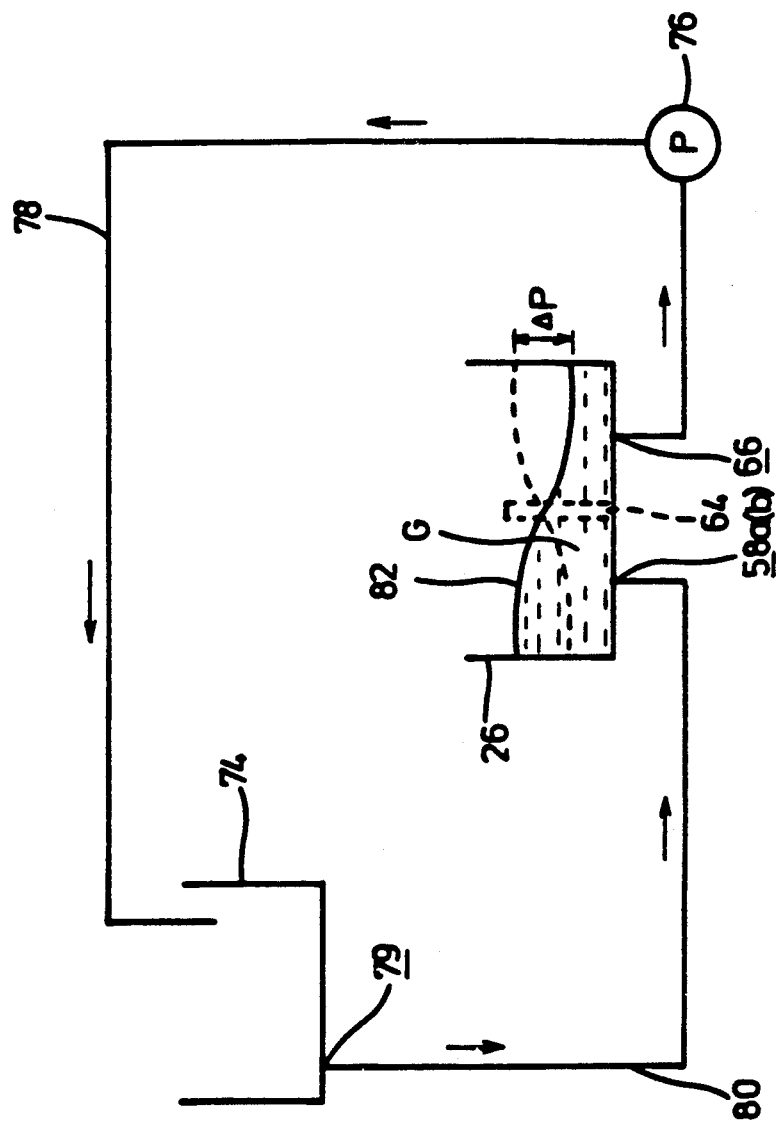

BLOOD STORAGE TANK

This application is a continuation of application Ser. No. 07/196,049, filed May 19, 1988, now abandoned.

BACKGROUND OF THE INVENTION

The present invention relates to a blood reservoir for temporarily storing blood in an extracorporeal blood circulating circuit, and more particularly to a blood reservoir which has a housing including a substantially vertical partition for suppressing resonant vibration of the surface level of blood stored in the blood reservoir upon pulsatory blood feed at the time of discharging the blood.

When a thoracic operation, for example, is to be carried out on a patient, an extracorporeal blood circulating circuit is established using an artificial lung in which the blood is circulated for an exchange of carbon dioxide and oxygen. The blood delivered from the artificial lung is temporarily stored in a blood reservoir for removal of air bubbles from the blood and a steady supply of the blood. Thereafter, the blood is pumped into the patient under the operation at a constant pulse rate.

Blood reservoirs for use in extracorporeal blood circulation include a closed-type blood reservoir in the form of a soft bag for storing blood in an airtight condition and an open-type blood reservoir in the form of a hard housing for storing blood. The open-type blood reservoir is advantageous in that priming and confirmation of the stored amount of blood can easily be performed, and it would be easy to construct the blood reservoir as a unitary component of an artificial lung. An artificial lung with centralized functions, employing an open-type blood reservoir has been proposed by the applicant (see Japanese Laid-Open Patent Publication No. 59-57661).

FIG. 1 of the accompanying drawings schematically illustrates a extracorporeal blood circulating circuit employing an open-type blood reservoir. A blood reservoir 2 stores blood B supplied from an artificial lung (not shown). The blood B is delivered out of the blood reservoir 2 from a blood discharge port 6 defined in the bottom of the reservoir 2 and through a flexible pipe 8. The flexible pipe 8 extends through a pump 10 which includes a rotor 12 that rotates in the direction of the arrows for pulsatively feeding the blood B through the flexible pipe 8 at a certain pulse rate.

The surface level 14 of the blood B stored in the blood reservoir 2 may be subjected to resonant vibration as indicated by the solid and broken lines due to various conditions or parameters such as the pulse rate of the pump 10, i.e., the speed of rotation of the rotor 12, the amount of the blood or the area of the surface level of the blood stored in the blood reservoir 2, and the viscosity of the blood B. When the blood B undergoes such resonant vibration, unwanted vibration tends to be applied to the artificial lung and other components of the extracorporeal blood circulating circuit. The amplitude of the resonant vibration is particularly large if the blood discharge port 6 is positioned asymmetrically with respect to the surface level 14. To avoid this shortcoming, the blood discharge port 6 should preferably be located substantially centrally in the blood reservoir 2. With the blood discharge port 6 thus positioned, however, the configuration and other design factors of the blood reservoir 2 are greatly limited.

SUMMARY OF THE INVENTION

It is a primary object of the present invention to provide a blood reservoir for temporarily storing blood in an extracorporeal blood circulating circuit, the blood reservoir including a substantially vertical partition for suppressing resonant vibration of the surface level of stored blood which would otherwise be caused by pulsatory blood discharge, so that unwanted vibration will not be applied to the extracorporeal blood circulating circuit, and an artificial lung and other components coupled to the blood reservoir can be arranged with greater freedom.

Another object of the present invention is to provide a blood reservoir comprising a blood storage section for temporarily storing blood, a blood discharge port defined in a bottom of the blood storage section for discharging the blood, the blood discharge port being displaced from a central portion of the blood storage section, and at least one partition disposed substantially vertically in the blood storage section for suppressing resonant vibration of a surface level of the stored blood upon pulsative blood discharge from the blood storage section.

Still another object of the present invention is to provide a blood reservoir wherein the partition comprises a plurality of substantially vertical plates extending in perpendicular relation to each other.

Yet still another object of the present invention is to provide a blood reservoir wherein the partition comprises a plurality of substantially vertical plates which substantially divide the blood storage section into a plurality of regions.

A further object of the present invention is to provide a blood reservoir wherein the blood storage section is of a tapered configuration with its volume progressively smaller toward the blood discharge port, the partition being disposed on a slanted surface of the tapered blood storage section.

A still further object of the present invention is to provide a blood reservoir wherein the partition has a height which is at least 80% of the height of the surface level of the stored blood which would be subjected to resonant vibration if the partition were dispensed with.

A yet still further object of the present invention is to provide a blood reservoir wherein the partition divides the blood storage section with a gap being left between the partition and an inner wall surface of the blood storage section.

Another object of the present invention is to provide a blood reservoir wherein the partition substantially divides 30% to 90% of the blood storage section.

Another object of the present invention is to provide a blood reservoir wherein the partition substantially divides 60% of the blood storage section.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 5 is a schematic view of a blood circulation experimenting circuit for showing the characteristics of the blood reservoir of the invention.

DETAILED DESCRIPTION OF THE PREFERRED EMBODIMENTS

Figure 1:
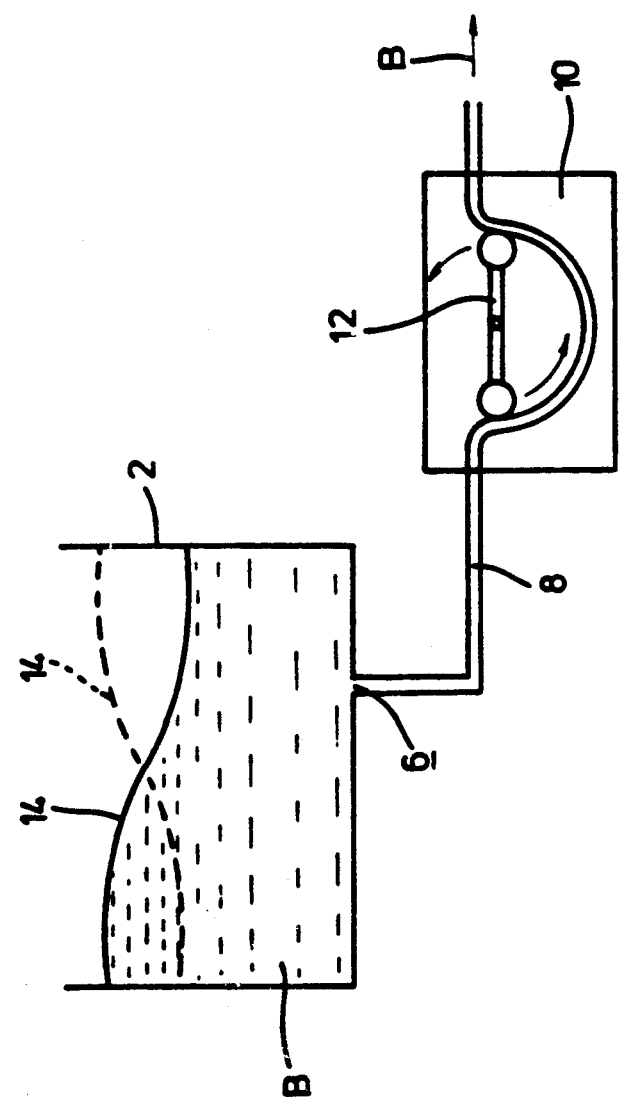
FIG. 1 is a schematic elevational view of a extracorporeal blood circulating circuit employing a blood reservoir shown as a comparative example.
Figure 2:
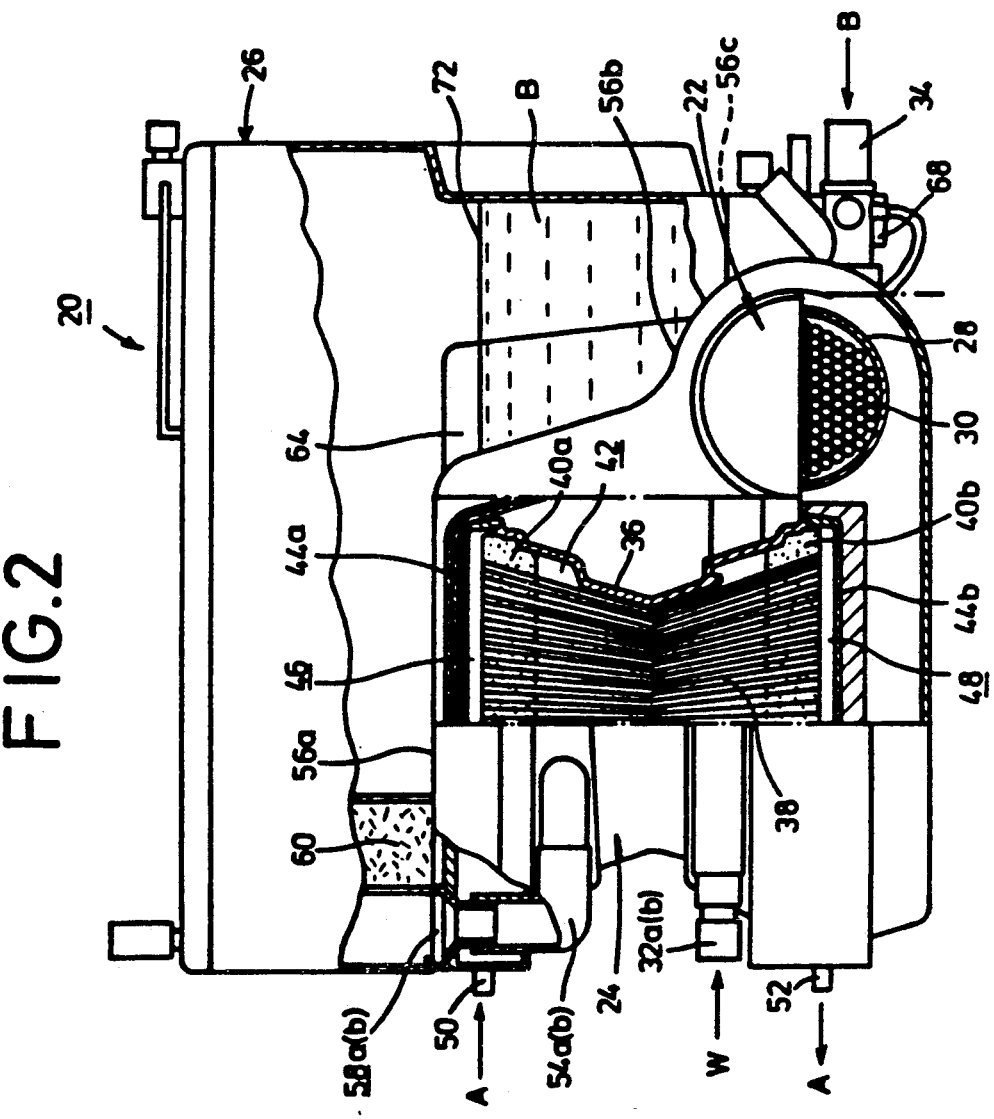
FIG. 2 is a schematic elevational view, partly in cross section, of a blood reservoir according to the present invention, coupled to an artificial lung.
Figure 3:
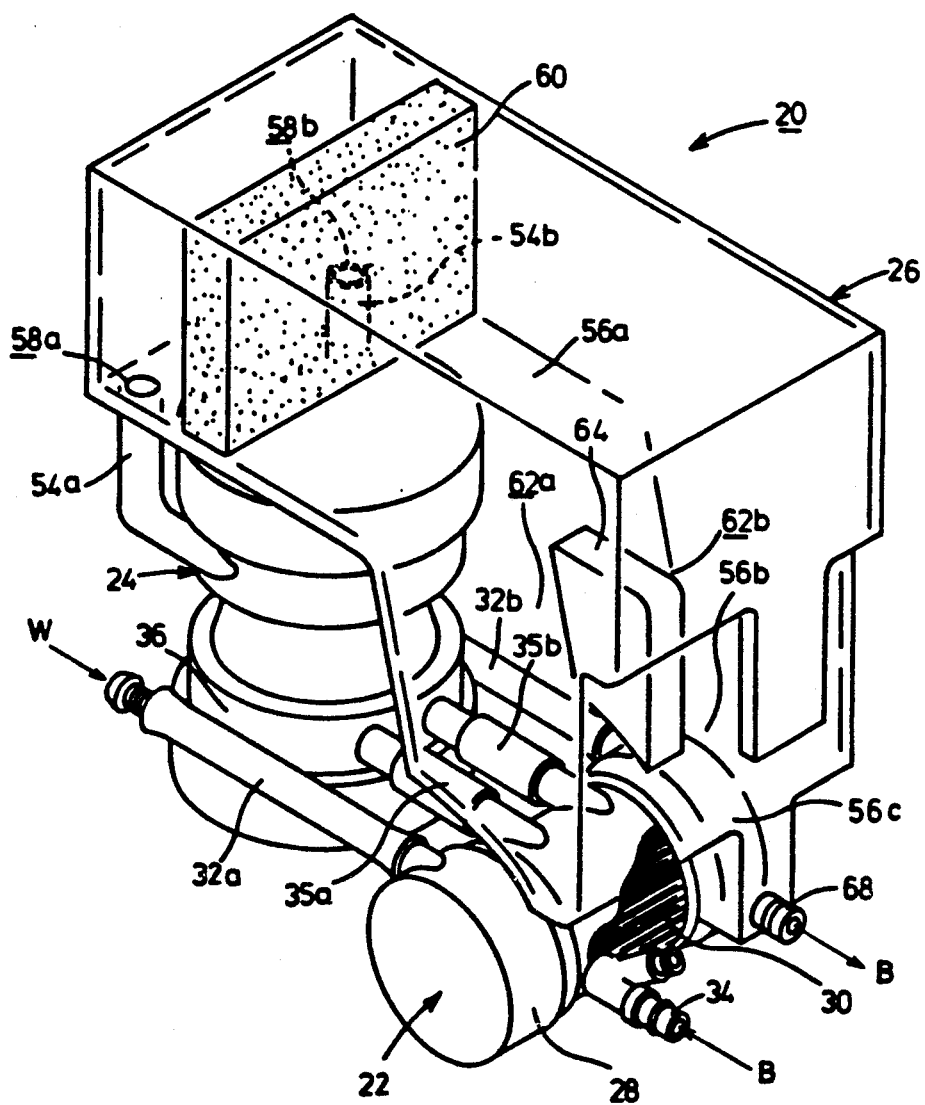
FIG. 3 is a schematic perspective view of the blood reservoir illustrated in FIG. 2.

As shown in FIGS. 2 and 3, an extracorporeal blood circulating apparatus has a unitary apparatus assembly 20 comprising a heat exchanger 22, an artificial lung 24, and an open-type blood reservoir 26 according to the present invention.

The heat exchanger 22 includes a tubular housing 28 accommodating therein a number of heat exchanger pipes 30. Warm or cold water W is supplied from a water port 32a to the pipes 30, and then discharged from the pipes 30 via a water port 32b. Blood B flowing from a blood supply port 34 into the heat exchanger 22 is heated or cooled to a prescribed temperature while it is passing around the pipes 30. Thereafter, the blood B is supplied via two joint tubes 35a, 35b (see FIG. 3) to the artificial lung 24.

The artificial lung 24 serves to remove carbon dioxide from the blood B and add oxygen to the blood B. The artificial lung 24 includes a multiplicity of hollow filamentary membranes 38 bundled and stored in a substantially cylindrical housing 36 with a constricted central portion. On the upper and lower ends of the housing 36, there are mounted partitions 40a, 40b holding the opposite ends of the hollow filamentary membranes 38. The housing 36 and the partitions 40a, 40b jointly define a space surrounded thereby and housing the hollow filamentary membranes 38 therein, the space communicating with the heat exchanger 22. This space serves as a gas exchanging chamber 42 through which the blood B flows. Covers 44a, 44b are also mounted on the upper and lower ends of the housing 36. The partition 40a and the cover 44a define a gas supply chamber 46 therebetween, and the partition 40b and the cover 44b define a gas discharge chamber 48 therebetween. The hollow filamentary membranes 38 are supplied with a gas A containing oxygen from a gas inlet port 50 via the gas supply chamber 46. The gas A delivered from the hollow filamentary membranes 38 is discharged through the gas discharge chamber 48 from a gas outlet port 52.

Figure 4:
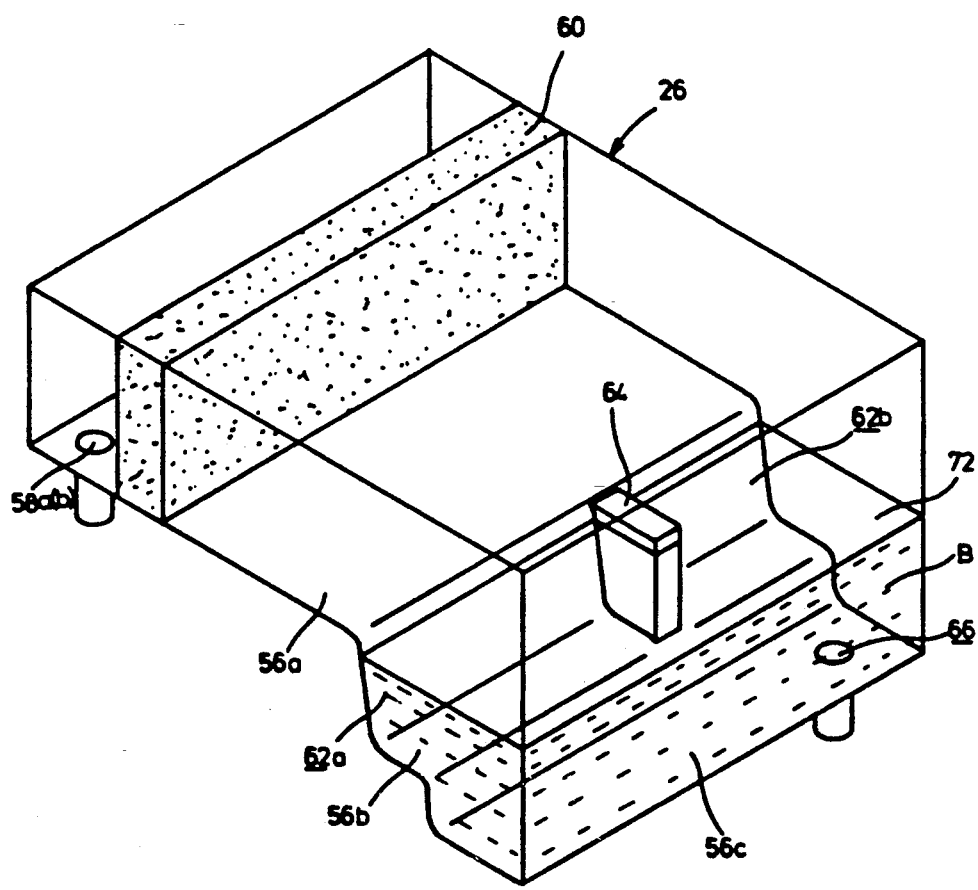
FIG. 4 is a schematic perspective view of the blood reservoir shown in FIGS. 2 and 3.

The blood reservoir 26 is held in communication with the gas exchanging chamber 42 of the artificial lung 24 through joint tubes 54a, 54b. As schematically shown in FIG. 4, the blood storage tank 26 has a bottom plate composed of first through third steps 56a, 56b, 56c. The joint tubes 54a, 54b have blood inlet ports 58a, 58b, respectively, opening at the first uppermost step 56a. A urethane anti-foaming member 60 is disposed on the first step 56a near the blood inlet ports 58a, 58b for preventing the blood B as it flows in from being foamed. A partition (baffle plate) 64 is mounted substantially centrally on the second intermediate step 56b and divides the blood storage space on the second step 56b into a first blood storage region 62a and a second blood storage region 62b. A blood discharge port 66 for discharging the blood B stored in the blood reservoir 26 opens at the end of the third lowermost step 56c. In operation, the blood discharge port 66 communicates with a pump (not shown) which delivers the blood at a prescribed pulse rate through a blood outlet port 68. In the case, the pump may be a rotary type or peristaltic finger type.

The blood reservoir of the invention is basically of the above structure. Now, operation and advantages of the extracorporeal blood circulating apparatus will be described below.

The blood B coming from the blood supply port 34 is supplied through the gaps between the tubes 30 stored in the heat exchanger 22 to the artificial lung 24. At this time, water W maintained at a prescribed temperature is flowing through the heat exchanger tubes 30 through the water ports 32a, 32b. The blood B is heated or cooled to a predetermined temperature by the water W flowing through the tubes 30.

The blood B fed from the heat exchanger 22 into the artificial lung 24 enters the gas exchanging chamber 42 surrounded by the housing 36 in which oxygen is added to the blood B and carbon dioxide is removed from the blood B. More specifically, the gas A containing oxygen is supplied into the bundled hollow filamentary membranes 38 in the housing 36 from the gas inlet port 50 through the gas supply chamber 46. Oxygen and carbon dioxide are exchanged in the blood B through the hollow filamentary membranes 38. The gas A containing carbon dioxide is discharged via the gas discharge chamber 48 from the gas outlet port 66.

The blood B to which oxygen has been added in the artificial lung 24 then flows through the joint tubes 54a, 54b and the blood inlet ports 58a, 58b into the blood reservoir 26. After air bubbles of foams contained in the blood B have been removed by the anti-foaming member 60, the blood B is stored in the blood reservoir 26.

The blood B stored in the blood reservoir 26 is then intermittently or pulsatively delivered out through the blood discharge port 66 by the pump (not shown) coupled to the blood outlet port 68. The surface level 72 of the blood B stored in the blood reservoir 26 would be subjected to resonant vibration due to intermittent delivery of the blood B by the pump. However, such resonant vibration is highly effectively suppressed by the partition 64 (which divides 60% of the blood storage section in the illustrated embodiment) on the second step 56b in the blood reservoir 26.

The effects of the partition 64 will be described in detail based on experimental results.

FIG. 5 schematically shows a blood circulation experimenting circuit employing the blood reservoir 26. A water storage tank 74 is disposed in a space above the blood reservoir 26. The blood discharge port 66 of the blood reservoir 26 is connected to the water storage tank 74 by a tube 78 through a pump 76 which can pulsatively feed water. The blood inlet port 58a (58b) of the blood reservoir 26 is connected to a discharge port 79 of the water storage tank 74 by means of a tube 80. Each of the blood reservoir 26 and the water storage tank 74 stores an aqueous solution G of 35% of glycerin having substantially the same property (the viscosity of about 3 centipoises) as that of blood B.

With the partition 64 removed from the blood reservoir 26, the aqueous solution G of glycerin was circulated by the pump 76 at a pulse rate of 100 beats/min.

The amount of change or fluctuation Δ P of the surface level 82 due to the pulsative blood feed was varied with respect to the amount of water stored in the blood reservoir 26 as indicated by the following Table 1:

TABLE 1

| Amount of stored water (ml) | Without partition P (mm) | With partition P (mm) |
|---|---|---|
| 1200 | 100 | 100 |
| 1100 | 150 | 100 |
| 1000 | 150 | 100 |
| 900 | 250 | 120 |
| 800 | 300 | 50 |
| 750 | 350 | 50 |
| 700 | 300 | 50 |
| 600 | 100 | 50 |

When the amount of water stored in the blood reservoir 26 was in the range of from 700 to 800 ml, the fluctuation Δ P of the surface level 82 was maximum, and the generation of resonant vibration was observed. When the partition 64 was substantially vertically mounted on the substantially central area of the second step 56b in the blood reservoir 26, as shown in FIG. 4, the fluctuation Δ P of the surface level 82 was greatly reduced and no resonant vibration was produced, as indicated by the Table 1.

More specifically, it is considered that resonant vibration which would otherwise be caused on the surface level 72 (see FIGS. 2 and 4) of the blood B stored in the blood reservoir 26 would be produced when the natural frequency of the blood storage system based on the characteristics of the blood B, the configuration of the reservoir tank 26, and other parameters coincides with the pulse rate of the pump. The pulse rate of the pump is selected to be in a certain range for practical reasons with respect to the artificial lung 24. The partition 64 located in the blood reservoir 26 is effective in making the system natural frequency widely different from the pulse rate of the pump, thus suppressing the undesirable resonant vibration. Therefore, when the pump is actuated, the surface level 72 of the blood B is kept calm without violent turbulent motion. Since the fluctuation Δ P of the surface level 72 arising from the pulse rate of the pump is small, the height of the surface level 72, i.e., the amount of the blood B stored in the blood reservoir 26 can easily and accurately be checked by a visual inspection. Moreover, inasmuch as any turbulent motion of the blood B in the blood reservoir 26 is effectively suppressed, vibration of the blood B is held to a minimum, and no unwanted vibration is applied to the apparatus. Since the interior space of the blood reservoir 26 is divided by the partition 64, it is not necessary to position the blood discharge port 66 centrally in the bottom of the blood reservoir 26. Accordingly, the artificial lung 24 and other components which are coupled to the blood reservoir 26 can be arranged with greater freedom.

Figure 6A:
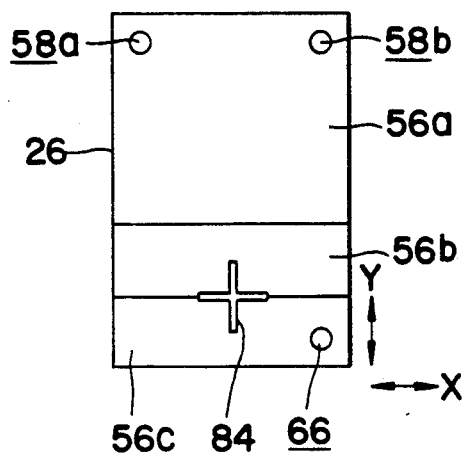
FIGS. 6(a) through 6(d) are schematic views of blood reservoir according to other embodiments of the present invention.
Figure 6B:
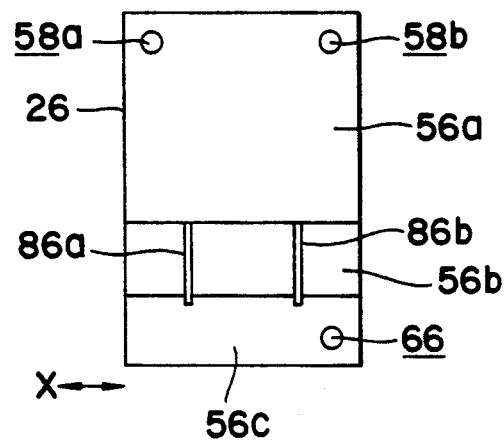
Figure 6C:
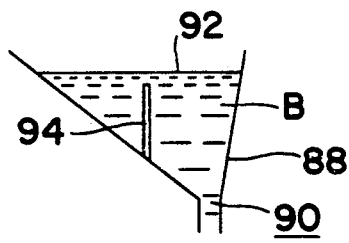
Figure 6D:
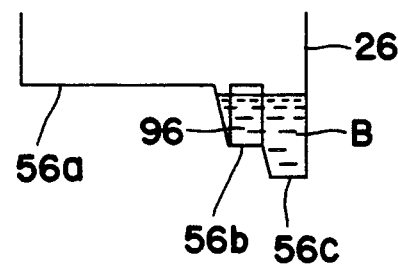

The blood reservoir 26 and the partition 64 are not limited to the above configurations, but may be of various shapes. For example, FIG. 6(a) shows a crisscross partition 84 mounted in the blood reservoir 26 for suppressing vibration of the blood B in X and Y directions. FIG. 6(b) illustrates two parallel partitions 86a, 86b mounted in the blood reservoir 26 and spaced in an X direction for particularly suppressing vibration in the X direction. FIG. 6(c) shows a blood reservoir 88 in the form of an inverted circular cone or an inverted pyramid, with a partition 94 disposed in the blood reservoir 88. The position of a blood discharge port 90 of the reservoir 88 is substantially at the center of the bottom of the blood storage region surrounded by the partition 94 and the righthand wall (as shown) of the reservoir 88 for effectively suppressing vibration of the blood B. FIG. 6(d) shows a partition 96 mounted on the second step 56b of the blood reservoir 26 shown in FIGS. 2 through 4 and held out of contact with the wall of the reservoir 26 at the second step 56b for reducing vibration of the blood B.

The partition 64 shown in FIGS. 2 and 3 is not limited to a certain cross-sectional shape insofar as it can sufficiently withstand the pressure of the blood stored in the blood reservoir 26. The partition 64 may be integrally formed with the blood reservoir 26. Therefore, the partition 64 can easily be manufactured. The height of the partition 64 should be at least 80% of the height of the surface level 72 which would be subjected to resonant vibration if the partition 64 were dispensed with. The partition 64 should be of as wide an area as possible for effective suppression of vibration of the blood B. The partition 64 should be of such a size as to divide 30% to 90% of the blood storage section in the blood reservoir 26. If the partition 64 divides 30% or more of the blood storage section, it can sufficiently suppress vibration of the blood. If the partition 64 divides 90% or less of the blood storage section, and where the blood discharge port is defined in one of the divided areas of the blood storage section, the blood can flow sufficiently between the divided areas, and hence it is not necessary to add extra blood to one of the divided areas which has the blood discharge port in order to compensate for a blood shortage in that divided area. Moreover, the possibility of resonant vibration in that divided area only is eliminated.

With the present invention, as described above, the blood reservoir for temporarily storing blood in the extracorporeal blood circulating apparatus intermittently delivers out the stored blood through the blood discharge port defined in the bottom of the reservoir, and the blood reservoir has the substantially vertical partition disposed therein. The partition is effective in making the system natural frequency, which is determined by the shape of the blood reservoir and the properties of the blood, widely different from the pulse rate at which the blood is delivered from the blood reservoir. Therefore, the surface level of the stored blood is free from resonant frequency. As a result, unwanted vibration is prevented from being applied to the extracorporeal blood circulating circuit. Since the blood discharge port of the blood reservoir can be positioned considerably freely, the artificial lung and other components coupled to the blood reservoir can also be arranged with greater freedom.

The present invention is not limited to the illustrated embodiment, but the principles of the invention are also applicable to a extracorporeal blood circulating apparatus which has no pump, or a blood reservoir which is separate from an artificial lung or a heat exchange, for example.

Although certain preferred embodiments have been shown and described, it should be understood that many changes and modifications may be made therein without departing from the scope of the appended claims.

What is claimed is:

1. A blood reservoir comprising: a blood storage section for temporarily storing blood including a bottom surface comprising an uppermost substantially horizontal portion, a lowermost substantially horizontal portion, and vertically inclined portions located therebetween a blood discharge port defined in said lowermost substantially horizontal portion of said blood storage section for discharging blood from said blood storage section, said inclined portions arranged for smoothly leading blood stored therein toward said blood discharge port, and a top positioned opposite said bottom surface, a blood inlet port defined in said uppermost substantially horizontal portion thereof, an antifoaming member disposed on said uppermost substantially horizontal portion of said bottom surface adjacent said blood inlet port and at least one baffle plate extending along at least a portion of said inclined portions within said blood storage section, said at least one baffle plate extending toward the top so as to be substantially vertically positioned, wherein said at least one baffle plate contacts said blood storage section only along said bottom surface such that blood stored in said blood storage section is kept in contact with oppositely positioned side faces of said at least one baffle plate at substantially the same level in order to suppress resonant vibration on a surface of blood caused by pulsative discharge of blood through the blood discharge port.

2. A blood reservoir according to claim 1, wherein a gap exists between said at lest one baffle plate and the top of the reservoir, between said at least one baffle plate and oppositely positioned sides of the reservoir, and between said at least one baffle plate and oppositely positioned ends of the reservoir.

3. A blood reservoir according to claim 1, wherein said at least one baffle plate defines a divided region extending across a width of said blood storage section, wherein the volume of said divided region equals 30% to 90% of the total volume of said blood storage section.

4. A blood reservoir according to claim 3, wherein said at least one baffle plate defines a divided region extending across a width of said blood storage section, wherein the volume of said divided region equals 60% of the total volume of said blood storage section.

5. A blood reservoir according to claim 1, wherein said bottom surface further includes a middle substantially horizontal portion disposed vertically between said uppermost and lowermost substantially horizontal portions said at least one baffle plate being placed on said middle substantially horizontal portion.

6. An apparatus for blood storage comprising: a blood storage section, including a bottom surface comprising an uppermost substantially horizontal portion, a lowermost substantially horizontal portion, and vertically inclined portions located therebetween, a blood discharge port defined in said lowermost substantially horizontal portion of said storage section, said blood discharge port being connected in fluid communication with a pulsatory pumping means for pulsatively delivering blood from the blood storage section at a prescribed pulse rate, said inclined portions arranged for smoothly leading blood stored therein toward said blood discharge port, and a top wall positioned opposite said bottom surface, a blood inlet port defined in said uppermost substantially horizontal portion thereof and at least one baffle plate extending along at least a portion of said inclined portions within said blood storage section, said at least one baffle plate extending towards the top wall of the blood storage section so as to be substantially vertically positioned, wherein said at least one baffle plate contacts said blood storage section only along said bottom surface such that blood stored in said blood storage section is kept in contact with oppositely positioned side faces of said at least one baffle plate at substantially the same level for suppressing resonant vibration of a surface level of blood upon pulsatile blood discharge from said blood storage section at said prescribed pulse rate through said blood discharge port as a result of operation of the pulsatory pumping means.

7. The apparatus according to claim 6, wherein said blood storage section includes two oppositely positioned side walls and an end wall, said at least one baffle plate being spaced from said top wall, said oppositely positioned side walls and said end wall so that blood can flow between a top face of said at least one baffle plate and the top wall of the blood storage section, between a front face of said at least one baffle plate and the end wall of the blood storage section which faces the front face of the at least one baffle plate, and between oppositely positioned side faces of said at least one baffle plate and the side walls of the blood storage section which face the side faces.

8. The apparatus according to claim 6, wherein said at least one baffle plate includes two baffle plates arranged in a crisscross fashion with respect to one another.

9. The apparatus according to claim 6, wherein said at least one baffle plate includes two spaced apart baffle plates arranged substantially parallel to one another.

10. The apparatus according to claim 6, wherein said blood inlet port is positioned adjacent one end wall of the apparatus and said blood outlet port is positioned adjacent an oppositely positioned end wall of the apparatus, said at lest one baffle plate having oppositely positioned end faces, one of said end faces facing one of the end walls but being spaced therefrom and the other end face facing the oppositely positioned end wall but being spaced therefrom, said at least one baffle plate lying in a plane that intersects the end walls.

11. The apparatus according to claim 6, wherein the bottom surface of the blood storage section defines a portion of the bottom of the apparatus, said blood inlet port being disposed elevationally higher than said blood outlet port, at least a portion of said at least one baffle plate being disposed elevationally lower than the blood inlet port and elevationally higher than the blood outlet port.

12. The apparatus according to claim 6, wherein said blood inlet port is positioned adjacent one end wall of the apparatus and said blood outlet port is positioned adjacent an oppositely positioned end wall of the apparatus, said apparatus including oppositely positioned side walls that extend between the end walls, said at least one baffle plate suppressing vibration of blood in a direction generally perpendicular to the side walls.

13. The apparatus according to claim 12, wherein said at least one baffle plate is positioned such that said at least one baffle plate also suppresses vibration of blood in a direction generally parallel to the side walls.

14. In a blood circulating apparatus that includes an oxygenator for oxygenating blood, a heat exchange fluidly connected to the oxygenator for changing the temperature of blood, and a blood reservoir fluidly connected to one of said oxygenator and said heat exchange, said blood reservoir comprising: a blood storage section for temporarily storing blood including a bottom surface comprising an uppermost substantially horizontal portion, a lowermost substantially horizontal portion, and vertically inclined portions located therebewteen a blood discharge port defined in said lowermost substantially horizontal portion of the blood storage section for discharging blood, said inclined portions arranged for smoothly leading blood stored therein toward said blood discharge port, and a top positioned opposite said bottom surface, a blood inlet port defined in said uppermost substantially horizontal portion thereof; and means for suppressing resonant vibration of a surface level of stored blood upon pulsatile blood discharge from the blood storage section, said means for suppressing including at least one baffle plate extending toward the top of the blood storage section so as to be disposed substantially vertically in said blood storage section, said at lest one baffle plate extending along at least a portion of said inclined portions, wherein said at least one baffle plate contacts said blood storage section only along said bottom surface such that blood stored in said blood storage section is kept in contact with oppositely positioned side faces of said at least one baffle plate at substantially the same level.

15. The apparatus according to claim 14, wherein said at least one baffle plate includes a flat plate which lies in a plane, said plane intersecting oppositely positioned end walls of said reservoir, said flat plate having an end face that faces one of the end walls but is spaced therefrom.

* * * * *

UNITED STATES PATENT AND TRADEMARK OFFICE
CERTIFICATE OF CORRECTION

PATENT NO.   :   5,196,166
DATED        :   March 23, 1993
INVENTOR(S)  :   Yoshiro KATSURA It is certified that error appears in the above-identified patent and that said Letters Patent is hereby corrected as shown below:

In Column 3, line 12, delete "reservoir" and insert -- reservoirs --.

In Column 3, line 59, delete "storage tank" and insert -- reservoir --.

Signed and Sealed this

Sixteenth Day of November, 1993

Attest:

BRUCE LEHMAN

Attesting Officer        Commissioner of Patents and Trademarks